United States Patent [19]

Salmond

[11] 3,941,787
[45] Mar. 2, 1976

[54] 1,4-DISUBSTITUTED-5,8-METHANO-TETRAHYDRO-QUINAZOLINONES

[75] Inventor: William G. Salmond, Kalamazoo, Mich.

[73] Assignee: Sandoz, Inc., E. Hanover, N.J.

[22] Filed: July 22, 1974

[21] Appl. No.: 491,170

[52] U.S. Cl............ 260/251 A; 260/566 R; 424/251
[51] Int. Cl.² .................................... C07D 239/70
[58] Field of Search ............................. 260/251 A

[56] References Cited
UNITED STATES PATENTS
3,563,990  2/1971  Hardtmann .................. 260/251

OTHER PUBLICATIONS
Polonovski et al., Chemical Abstracts, Vol. 42, 5855a (1948).

Primary Examiner—Donald G. Daus
Assistant Examiner—Diana G. Rivers
Attorney, Agent, or Firm—Gerald D. Sharkin; Richard E. Vila

[57] ABSTRACT

Anti-inflammatory agents of the formula I:

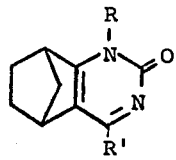

I wherein
R is lower alkyl, cycloalkyl or cycloalkylalkyl,
R' is a radical of the formula

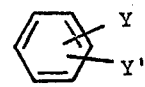

in which Y and Y' are hydrogen, lower alkyl, lower alkoxy, halo or trifluoromethyl, or a radical of the formula

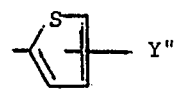

in which Y'' is hydrogen, halo or alkyl,
are prepared by cyclizing a compound of formula II

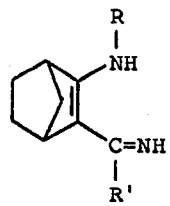

II in which R and R' are as defined above, with phosgene.

10 Claims, No Drawings

,4-DISUBSTITUTED-5,8-METHANO-TETRAHYDRO-QUINAZOLINONES

This invention relates to compounds which are 1-substituted-4-cyclosubstituted-5,8-methano-tetrahydro inazolinones and intermediates therefor and to ethods and compositions utilizing the pharmacological properties of these compounds.

The compounds of this invention have the formula I:

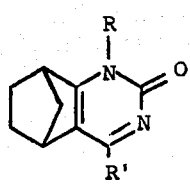

I

1erein:
R is lower alkyl of 1 to 6 carbon atoms, cycloalkyl of 3 to 8 carbon atoms or cycloalkylalkyl of 4 to 10 carbon atoms in which the cycloalkyl is of 3 to 8 carbon atoms and the alkyl of 1 to 3 carbon atoms,
R' is a radical of the formula

which Y and Y' are the same or different and reprent hydrogen, halo of atomic weight of 18 to 36, lower kyl, preferably containing from 1 to 2 carbon atoms, g., methyl or ethyl, lower alkoxy, preferably containg from 1 to 2 carbon atoms, e.g., methoxy or ethoxy, · one of Y and Y' is trifluoromethyl while the other is /drogen, or a radical of the formula

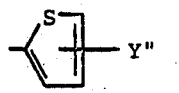

which Y'' is hydrogen, halo of atomic weight of from 3 to 36, i.e., fluorine, chlorine, or alkyl of 1 to 3 carbon atoms. This invention also comprises:
a. preparing a compound of the formula I, above, by /clizing a compound of formula II

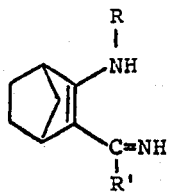

II 1 which R and R' are as defined above, with phosgene, nd
b) preparing a compound of the formula Ia

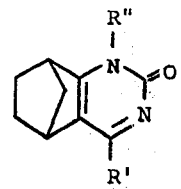

Ia in which R' is as defined above, and R'' has the same significance as R, defined above, except that it may not signify a tertiary alkyl group in which the tertiary carbon atom is directly attached to the ring nitrogen atom, by cyclizing a compound of formula IIa

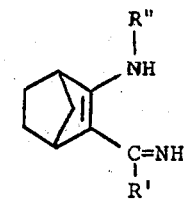

IIa wherein R' and R'' are as defined above with a carbonic acid derivative selected from the group of
i, a $C_{1-2}$ alkyl chlorocarbonate and
II, a 1,1'-carbonyldiimidazole.

Process a) is suitably carried out at a temperature of from −30°C. to +50°C., preferably −5°C. to 30°C. The reaction may be carried out in an organic solvent which is inert under the reaction conditions, suitably an aromatic hydrocarbon, e.g., benzene, toluene or xylene, preferably toluene. Other suitable solvents include dioxane. The mole ratio of the phosgene to the compound of formula II is not particularly critical, but a substantial excess of the phosgene is preferably employed. The process may optionally be carried out in the presence of an acid-binding agent such as an organic base, e.g., a trialkylamine or pyridine, preferably triethylamine. The reaction time may range for ½ to 10 hours, more usually 1 to 4 hours.

Process b) (i) is suitably carried out at a temperature of from −30°C. to 100°C., preferably −0°C. to +30°C. The reaction may be carried out in an organic solvent which is inert under the reaction conditions, suitably an aromatic hydrocarbon, e.g., benzene, toluene or xylene, preferably toluene. Other suitable solvents include dioxane or the alkyl chlorocarbonate. The mole ratio of the chlorocarbonate to the compound of formula IIa is not particularly critical, but a substantial excess of the alkyl chlorocarbonate is preferably employed. The process may optionally be carried out in the presence of an acid-binding agent such as an organic base, e.g., a trialkylamine or pyridine, preferably triethylamine.

Process b) (ii) is suitably carried out at a temperature of from 0°C. to 120°C., preferably 40°C. to 90°C. The reaction is preferably carried out in an organic solvent which is inert under the reaction conditions, suitably an aromatic hydrocarbon, e.g., benzene, toluene or xylene, especially benzene. An excess of 1,1'-carbonyldiimidazole is preferably employed.

The compounds of the formula I and Ia can be isolated from the reaction mixtures by working up by conventional procedures.

The compounds of formula II above can be prepared by reacting a compound of formula III

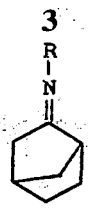

in which R is as defined above with a suitable strong base and a compound of formula IV $$R'-C \equiv N \qquad \text{IV}$$

in which R' is as defined above, in an inert solvent to form a solution of the Salt A

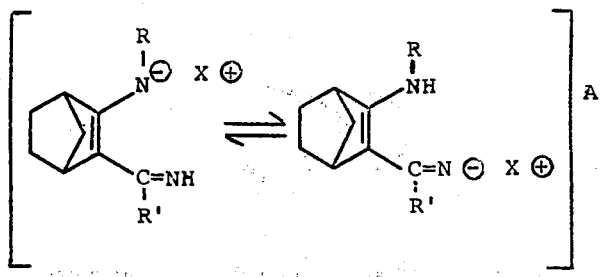

in which R and R' are as defined above, and X is a metal, preferably lithium or magnesium, and quenching the solution with water.

Suitable strong bases are those which are capable of removing a hydrogen atom from the methylene group in the ring adjacent to the amine function of compound III to provide the desired anion for reaction with the compound of formula IV. They include the alkali metal salts, especially the lithium salt, of secondary amines such as diethylamine, dimethylamine and diisopropylamine, as well as other bases such as methyl magnesium iodide. One mol of the strong base and up to about 1.2 mols can be used per mol of the compound of formula III, preferably equimolar amounts are used.

The temperature of the reaction mixture is maintained at about 20° to 80°C.

Generally, the compound of formula III in a suitable solvent, such as benzene, is added to a solution of the base in a suitable solvent and allowed to react for about 10 to 60 minutes. The compound of formula IV, neat or in a suitable inert solvent, is then added to the reaction mixture of the base and compound III. The compounds III and IV and the strong base may, however, be brought together simultaneously.

The resulting reaction mixture containing the salt of formula A can, at this point, be treated by process a) and b) above to yield directly the compound of formula I. Suitable temperature control should be exercised, at this reaction is more exothermic than when compound II is employed. However, the salt solution is advantageously quenched with water to obtain the compound of formula II, which can be reacted in situ according to process a) or b) to form compound I, but is preferably extracted and washed first using conventional methods.

The compounds of formula III can be prepared by reacting compound of formula V

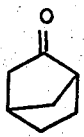

with a compound of formula VI $$R-NH_2 \qquad \text{VI}$$

wherein R is as defined above, to eliminate one molecule of water, conveniently in the presence of a molecular sieve or a dehydrating agent, such as alumina, calcium chloride, phosphorus pentoxide or mixtures thereof.

This reaction can be carried out at temperatures from 0° to about 80°C., conveniently 20° to 30°C. In cases where the compound of formula VI is volatile, an excess is generally mixed with the compound of formula V and the unreacted portion removed by vacuum distillation after removal of the dehydrating agent. When the compound of formula VI is non-volatile, equimolar proportions of compounds of formulae V and VI are mixed in suitable solvent such as benzene, the solvent then being removed in vacuo after completion of the reaction and after filtration of the dehydrating agent.

The compound of formula V is known.

The compounds of formula I are useful because they possess pharmaceutical activity in animals. In particular, the compounds I are useful as anti-inflammatory agents as indicated by the Carrageenan-induced edema test in rats on oral administration (20–180 mg./kg.). For the abovementioned use, the dosage administered will, of course, vary depending upon known factors such as the particular compound used and mode of administration. However, in general, satisfactory results are obtained when administered at a daily dosage of from about 4 milligrams to about 200 milligrams per kilogram of body weight, preferably given in divided doses 2 to 4 times a day, or in sustained release form. For most mammals the administration of from about 280 milligrams to about 2000 milligrams of the compound per day provides satisfactory results and dosage forms suitable for internal administration comprise from about 70 milligrams to about 1000 milligrams of the compound in admixture with a solid or liquid pharmaceutical carrier or diluent.

The compounds of the formula I are also useful as analgesics as indicated by application of pressure to yeast-inflammed foot of the rat (oral administration). For such use, the compound may be administered to obtain satisfactory results in modes and forms similar to those employed in the treatment of inflammation and at dosages indicated above as applicable for the use of the compound in the treatment of inflammation.

For the above usage, oral administration with pharmaceutically acceptable carriers may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents, and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of administration are solid compositions, particularly hardfilled capsules and tablets.

A representative formulation is a capsule prepared by conventional techniques and containing the following ingredients:

| Ingredient | Parts by Weight |
| --- | --- |
| Compound of formula I, e.g., 1-isopropyl-4-phenyl-5,8-methano-5,6,7,8-tetrahydro-2(1H)-quinazolinone | 50 |
| Inert solid diluent, e.g., kaolin | 200 |

Preferred compounds of formula I, from the point of view of pharmacological activity, are those in which R signifies an isopropyl radical.

The following examples show representative compounds encompassed within the scope of this invention and the manner in which such compounds are prepared. However, it is to be understood that the examples are for purposes of illustration only.

EXAMPLE 1

5,6,7,8-Tetrahydro-1-isopropyl-4-phenyl-5,8-methano-quinazolin-2(1H)-one.

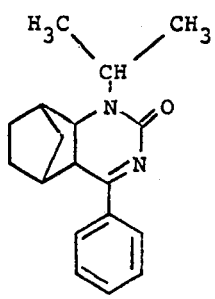

STEP A: N-isopropyl-2-norbornylidene imine

A mixture of 44 g. of norbornanone, 50 g. of isopropylamine, 40 ml. of hexane and 50 g. Linde Type 3A molecular sieves is allowed to stand for 17 hours at room temperature, after which the solids are removed by filtration and the excess of isopropylamine is removed in vacuo at room temperature to obtain N-isopropyl-2-norbornylidene imine.

STEP B:
2-isopropylamino-α-phenyl-1-norbornene-1-methylenimine

To n-butyl lithium (189.5 ml. of a 15% solution in hexane) 1 added a solution of 30.3 g. of diisopropylamine in 300 ml. benzene. After 15 minutes 45.3 g. of N-isopropyl-2-norbornylidene imine is added while stirring. After stirring for a further 15 minutes, 30 g. benzonitrile added dropwise and the mixture stirred for 20 minutes, producing a red solution of the lithium salt of 2-isopropylamino-α-phenyl-1-norbornene-1-methylenimine. The reaction mixture is then treated with 20 ml. of water to obtain a green solution containing 2-isopropylamino-α-phenyl-1-norbornene-1-methylenimine.

STEP C:
5,6,7,8-Tetrahydro-1-isopropyl-4-phenyl-5,8-methanoquinazolin-2(1H)-one.

To the solution of 2-isopropylamino-α-phenyl-1norbornene-1-methylenimine obtained in Step B, above, at 0°C. is added 200 ml. of a 12.5% solution of phosgene in benzene. The reaction mixture is stirred for 30 minutes, extracted with 2N hydrochloric acid and the acidic extract made basic with 50% sodium hydroxide solution. The basic solution is then extracted with methylene chloride and this extract dried, evaporated in vacuo and the residue crystallized from ether to obtain 5,6,7,8-tetrahydro-1-isopropyl-4-phenyl-5,8-methano-quinazolin-2(1H)-one, m.p. 188°–189°C.

EXAMPLE 2

Following the procedure of Example 1 the following additional compounds of the invention are prepared:
a. 5,6,7,8-tetrahydro-1-isopropyl-4-(4'-fluorophenyl)-5,8-methano-quinazolin-2(1H)-one.
b. 5,6,7,8-tetrahydro-1-isopropyl-4-(2-thienyl)-5,8-methano-quinazolin-2(1H)-one.
c. 5,6,7,8-tetrahydro-1-isopropyl-4-(3'-methoxyphenyl)-5,8-methano-quinazolin-2(1H)-one.
d. 5,6,7,8-tetrahydro-1-isopropyl-4-(3'-trifluoromethylphenyl)-5,8-methano-quinazolin-2(1H)-one.
e. 5,6,7,8-tetrahydro-1-isopropyl-4-(3',4'-dimethoxyphenyl)-5,8-methano-quinazolin-2(1H)-one.
f. 5,6,7,8-tetrahydro-1-cyclopropyl-4-phenyl-5,8-methano-quinazolin-2(1H)-one.
g. 5,6,7,8-tetrahydro-1-cyclopropylmethyl-4-(4'-fluorophenyl)-5,8-methano-quinazolin-2(1H)-one.

What is claimed is:
1. A compound of the formula

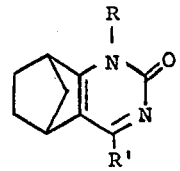

I wherein:
R is lower alkyl of 1 to 6 carbon atoms, cycloalkyl of 3 to 8 carbon atoms or cycloalkylalkyl of 4 to 10 carbon atoms in which the cycloalkyl is of 3 to 8 carbon atoms and the alkyl of 1 to 3 carbon atoms,
R' is a radical of the formula

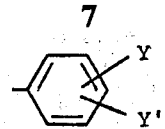

in which Y and Y' are the same or different and represent hydrogen, halo of atomic weight of 18 to 36, alkyl having from 1 to 2 carbon atoms, alkoxy having from 1 to 2 carbon atoms, or one of Y and Y' is trifluoromethyl while the other is hydrogen, or a radical of the formula

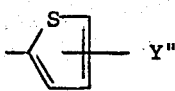

in which Y'' is hydrogen, halo of atomic weight of from 18 to 36 or alkyl of 1 to 3 carbon atoms.

2. A compound of claim 1 in which R' is phenyl or substituted phenyl.

3. A compound of claim 2 in which R' is phenyl.

4. A compound of claim 1 in which R is alkyl.

5. A compound of claim 4 in which R is isopropyl.

6. A compound of claim 2 in which R is isopropyl.

7. The compound of claim 6 in which R' is phenyl.

8. The compound of claim 6 in which R' is 4-fluorophenyl.

9. A compound of claim 1 in which R is cyclopropylmethyl.

10. The compound of claim 6 which is 1-isopropyl-4-phenyl-5,8-methano-5,6,7,8-tetrahydro-2(1H)-quinazolinone.

* * * * *